United States Patent [19]

Aya et al.

[11] 4,059,430
[45] Nov. 22, 1977

[54] ORGANIC (THIO) PHOSPHORIC ACID ESTER COMPOUNDS AND HERBICIDAL COMPOSITIONS

[75] Inventors: Masahiro Aya; Junichi Saito; Toyohiko Kume; Kazuomi Yasui, all of Tokyo, Japan

[73] Assignee: Bayer Aktiengesellschaft, Leverkusen, Germany

[21] Appl. No.: 725,614

[22] Filed: Sept. 22, 1976

[30] Foreign Application Priority Data

Oct. 22, 1975   Japan .................................. 50-126321

[51] Int. Cl.² .......................... A01N 9/36; G07F 9/09; G07F 9/165
[52] U.S. Cl. ............................................. 71/86; 71/87; 260/943
[58] Field of Search ....................... 260/943; 71/86, 87

[56] References Cited

U.S. PATENT DOCUMENTS

| | | | |
|---|---|---|---|
| 3,102,019 | 8/1963 | Speziale et al. | 260/943 X |
| 3,350,192 | 10/1967 | Richter | 71/87 |
| 3,385,689 | 5/1968 | Richter | 71/87 |

*Primary Examiner*—Richard L. Raymond
*Attorney, Agent, or Firm*—Burgess, Dinklage & Sprung

[57] ABSTRACT

New organic (thio) phosphoric acid ester compounds of the formula

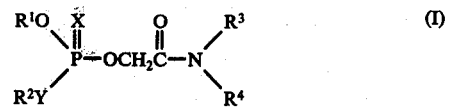

in which $R^1$ is $C_1$–$C_6$ alkyl, cyclohexyl, or phenyl,
$R^2$ is $C_1$–$C_6$ alkyl,
$R^3$ is $C_1$–$C_6$ alkyl,
$R^4$ is cyclohexyl or phenyl,
X is oxygen or sulfur, and
Y is oxygen or sulfur have been found to exhibit excellent herbicidal, particularly selective herbicidal activity.

32 Claims, No Drawings

ORGANIC (THIO) PHOSPHORIC ACID ESTER COMPOUNDS AND HERBICIDAL COMPOSITIONS

The present invention relates to certain new organic (thio) phosphoric acid ester compounds, to herbicidal compositions containing such compounds and to their use as herbicides.

It is known from U.S. Pat. No. 3,385,689 that the compound of the formula

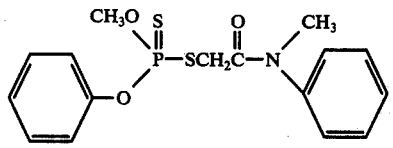

possesses herbicidal activity.

The present invention now provides, as new compounds, the organic (thio) phosphoric acid esters of the general formula

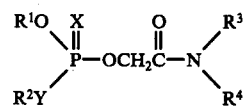

in which
$R^1$ is $C_1-C_6$ alkyl, cyclohexyl or phenyl,
$R^2$ is $C_1-C_6$ alkyl,
$R^3$ is $C_1-C_6$ alkyl,
$R^4$ is cyclohexyl or phenyl,
X is oxygen or sulphur, and
Y is oxygen or sulphur.

The compounds of the formula (I) have been found to exhibit excellent herbicidal activity.

Preferably $R^1$ is $C_1-C_4$ alkyl (namely, methyl, ethyl, n- or isopropyl or n-, iso-, sec.- or tert.-butyl), cyclohexyl or phenyl, $R^2$ is $C_1-C_4$ alkyl and $R^3$ is $C_1-C_4$ alkyl.

The present invention also provides a process for the preparation of a compound of the formula (I), in which (a) a phosphoryl chloride of the general formula

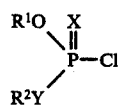

in which
$R^1$, $R^2$, X and Y have the meanings stated above,
is reacted with a glycolic acid amide of the general formula

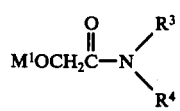

in which
$R^2$ and $R^4$ have the meanings stated above, and
$M^1$ is hydrogen or an alkali metal atom, preferably hydrogen, sodium or potassium or an ammonium group
or (b), provided Y is to be sulphur, a thiophosphate of the general formula

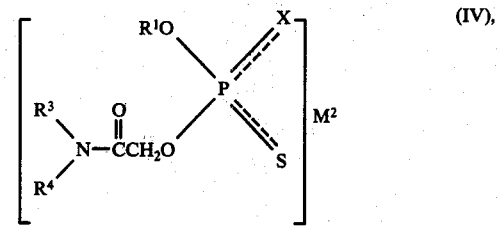

in which
$R^1$, $R^3$, $R^4$ and X have the meanings stated above, and
$M^2$ is an alkali metal atom or an ammonium group, preferably sodium, potassium or ammonium,
is reacted with a halide of the general formula

in which
$R^2$ has the meaning given above, and
Hal is a halogen atom, preferably chlorine or bromine.

When O-phenyl-O-ethylphosphoryl chloride and glycolic acid N-methylanilide are used as starting materials in process variant (a), the course of the reaction can be illustrated by the following equation:

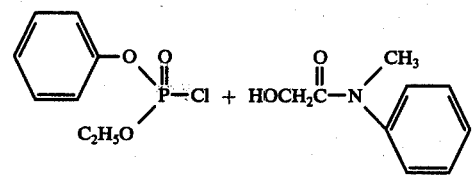

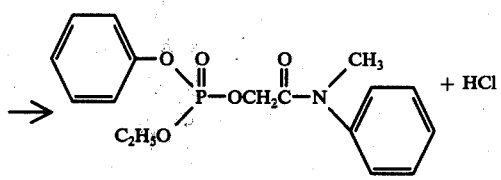

When potassium O-ethyl-O-(N-methyl-anilinocarbonylmethyl) thiophosphate and n-propyl chloride are used as starting materials in process variant (b), the course of the reaction can be illustrated by the following equation:

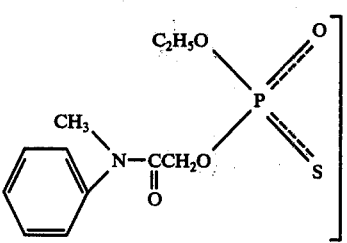

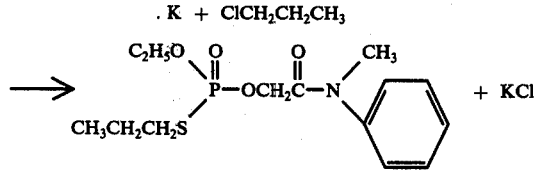

Examples of the phosphoryl chlorides of the formula (II) include O,O-diethylthionophosphoryl chloride, O,O-di-n-propylphosphoryl chloride, O,O-di-n-butylphosphoryl chloride, O-phenyl-O-ethylphosphoryl chloride, O-phenyl-O-ethylthionophosphoryl chloride, O-phenyl-O-n-propylphosphoryl chloride, O-phenyl-O-n-butylphosphoryl chloride, O-ethyl-S-n-propylthiolphosphoryl chloride, O-n-butyl-S-methylthiolphosphoryl chloride and O-cyclohexyl-S-methylthiolphosphoryl chloride.

Examples of the glycolic acid amides of the formula (III) include glycolic acid-N-methylanilide, glycolic acid-N-ethylanilide, glycolic acid-N-iso-propylanilide and glycolic acid-N-methyl-N-cyclohexylamide, as well as the potassium or sodium salts thereof.

Process variant (a) may be effected in the presence of an acid-binding agent, especially when $M^1$ is hydrogen. Any of the customary acid acceptors may be used for this purpose, for example a hydroxide, carbonate, bicarbonate or alcoholate of an alkali metal, or a tertiary amine, for example triethylamine, diethylaniline or pyridine.

Alternatively, the need for an acid-binding agent can be dispensed with, by employing the glycolic acid amide in the form of an alkali metal salt.

Examples of the thiophosphates of the formula (IV) include potassium, sodium or ammonium O-ethyl-O-(N-methylanilinocarbonylmethyl)thiophosphate, O-n-butyl-O-(N-methylanilinocarbonylmethyl)thiophosphate and O-cyclohexyl-O-(N-methylanilinocarbonylmethyl)thiophosphate.

Examples of the halides of the formula (V) include methyl chloride, methyl bromide, n-propyl chloride and n-propyl bromide.

The preparative process, whether variant (a) or variant (b), is preferably carried out in the presence of a solvent or diluent, preferably an inert organic solvent.

Examples of suitable solvents and diluents include water; aliphatic, alicyclic and aromatic hydrocarbons (which may be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, di-isopropyl ether, dibutyl ether, propylene oxide, dioxan and tetrahydrofuran; ketones such as acetone, methyl ethyl ketone, methyl isopropyl ketone, and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethyl formamide and dimethyl acetamide; and sulfones and sulfoxides such as dimethyl sulfoxide and sulfolane. Bases such as pyridine can serve as a solvent and, in process variant (a), also as acid-binding agents.

Both process variants can be carried out over a wide temperature range. Generally, the reaction is effected at temperatures between $-20°$ C and the boiling point of the mixture, preferably between 0° and 100° C. Furthermore, the reaction is preferably effected at normal pressures, although it is also possible to effect the reaction under an elevated or reduced pressure.

The compounds of the present invention exhibit an excellent weed-killing activity, especially against weeds that occur in paddy fields, or other crops such as soy beans, sugar beets, cotton, etc., for example gramineous weeds, broad-leaved weeds and perennial weeds. By "weeds" in the broadest sense are meant all unwanted plants growing in cultivated or uncultivated areas.

The present compounds are superior to conventional herbicides and to the structurally analogous compound of the formula (VI) in that they show an excellent selective herbicidal effect, when used in appropriate amounts, whether they are used in pre-emergence or in post-emergence treatments.

The present compounds, when used in appropriate amounts, exhibit little or no phytotoxicity towards crop plants, especially rice plants. In this respect they appear to be better than compounds such as PCP or NIP (2,4-dichlorophenyl-4'-nitrophenyl ether), which are widely used as herbicides in rice fields. The present compounds also show but little toxicity towards warm-blooded animals.

The present compounds exhibit a non-selective herbicidal action when used in large amounts (say, 6 – 30 kg of active compound per hectare) but exhibit excellent selective herbicidal action when used in smaller amounts (say, 0.1 – 6 kg per hectare).

Thus, they are active against the following: dicotyledons, such as *Rotala indica* Koehne, *Lindernia pyxidarius* L., and *Polygonum persicaria* L.; and monocotyledons, such as *Echinochloa crus-galli* Beauvois, *Monochoria vaginalis* Presl, *Eleocharis acicularis* L., *Cyperus microiria* Steudel, *Sagittaria pygmaea* Miquel, *Potamogeton distinctus* Bennett and *Alisma canaliculatum* Braun and Bouché.

Each of the above-named weeds is merely a typical example of its genus; the present compounds are effective against other species in the same genus.

The active compounds can be converted into the customary formulations, such as solutions, emulsions, wettable powders, suspensions, powders, dusting agents, foams, pastes, soluble powders, granules, aerosols, suspension-emulsion concentrates, and formulations used with burning equipment, such as fumigating cartridges, fumigating cans, fumigating coils and the like, as well as ULV (ultra-low-volume) cold mist and warm mist formulations.

These formulations may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

Adhesives such as carboxymethylcellulose and natural and synthetic polymers in the form of powders, granules or latices, such as gum arabic, polyvinyl alcohol and polyvinyl acetate, can be used in the formulations.

The active compounds according to the invention, as such or in their formulations, can (in order to reinforce and supplement their spectrum of action in accordance with the intended use) be combined with other herbicidal active compounds. The active compounds according to the invention can also be used as a mixture with other active compounds, such as fungicides, insecticides and acaricides.

The formulations in general contain 0.1 to 95 percent by weight of active compound, preferably 0.5 to 90 percent by weight.

The active compounds can be used as such, in the form of their formulations or in the application forms prepared therefrom, such as ready-to-use solutions, emulsions, suspensions, powders, pastes and granules. They may be applied in the customary manner, for example by spraying, atomising, dusting, scattering, mixing with soil, coating, fumigation, vaporising and watering.

The compositions may be diluted for actual application, and the amount of active compound used can vary within substantial ranges. In general, the ready-to-use preparations contain 0.01 to 20%, preferably 0.05 to 10%, by weight, of the active compound.

The active compounds can also be applied using the ULV method, whereby it is possible to apply compositions that are 95% by weight active compound or even to use the active compound by itself.

In general, the active compound is applied to an area of agriculture in an amount of 0.1 to 10 kg per hectare, preferably 0.3 to 6 kg per hectare. However, it is possible to employ application rates outside the broader range.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides means of yielding crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The herbicidal compositions of this invention are illustrated by the following Examples, in which the active compounds are identified by the number of the corresponding preparative Example. Parts are by weight.

EXAMPLE (I)

Fifteen parts of compound No.6, 80 parts of a mixture of siliceous earth and kaolin (at a ratio of 5:1) and 5 parts of an emulsifier (a polyoxyethylene alkylphenylether) were mixed by pulverization, thereby forming a wettable powder. The resulting wettable powder was diluted with water and applied by spraying.

EXAMPLE (II)

Thirty parts of compound No.11, 30 parts of xylene, 30 parts of methylnaphthalene and 10 parts of a polyoxyethylene alkylphenylether were mixed by stirring, thereby forming an emulsifiable concentrate. The resulting concentrate was diluted with water before being applied by spraying.

EXAMPLE (III)

Two parts of compound No.4 and 98 parts of a mixture of talc and clay (at a ratio of 1:3) were mixed by pulverization, thereby forming a dusting agent.

EXAMPLE (IV)

1.5 parts of compound No.13, 0.5 part of isopropyl hydrogen phosphate (PAP), and 98 parts of a mixture of talc and clay (at a ratio of 1:3) were mixed by pulverization, thereby forming a dusting agent.

EXAMPLE (V)

Twenty-five parts of water were added to a mixture comprising 10 parts of compond No.1, 10 parts of bentonite, 78 parts of a mixture of talc and clay (at a ratio of 1:3) and 2 parts of lignin sulfonate.

The resulting mixture was compacted well and then finely divided into granules of 20–40 mesh by means of an extruder granulator. The granules were dried at 40° – 50° C to form a granular agent.

EXAMPLE (VI)

Ninety-five parts of clay particles having a particle size distribution of 0.2 to 2 mm were charged into a rotary mixer, and 5 parts of compound No.12 dissolved in an organic solvent were sprayed on said particles in the mixer during rotation. After a homogeneous product had been formed, it was dried at 40° – 50° C to give a granular agent.

EXAMPLE (VII)

0.5 part of compound No.3, 20 parts of a mixture of high-boiling-point aromatic compounds and 79.5 parts of kerosine were mixed by stirring, thereby giving an oil preparation.

The herbicidal activity of the present compounds is illustrated by the following biotest Examples. Again, each of the compounds of this invention is identified by the number of the corresponding preparative examples.

EXAMPLE A

Pre-emergence treatment under flooded conditions against paddy-field weeds (pot test).

Production of the active-compound preparation
Solvent: 5 parts by weight of acetone Emulsifier: 1 part by weight of benzyloxypolyglycol ether The preparation of the active compound was obtained by mixing one part by weight of the active compound with the above-stated amounts of solvent and emulsifier. The emulsifiable concentrate obtained in this manner was then diluted with water to the required concentration.

Test method

Wagner pots (0.0002 are) were charged with soil from a paddy field. Two rice plants (Kinmaze variety) at the two-or three-leaved stage (about 10 cm high) were transplanted into each pot. In addition, *Echinochloa crus-galli,* Cyperus sp., *Eleocharis acicularis* L. and seeds of various broadleaved weeds (including *Monochoria vaginalis* Presl, *Rotala indica* Koehne, and *Lindernia pyxidaria* L.) were also planted and the whole was maintained in a wet condition. Two days after transplantation, each pot was flooded with water to a depth of 3 cm. The active-compound preparation was then applied at a prescribed dosage.

After this treatment, water was allowed to leak out of each pot for two days at a rate of 2–3 cm per day. Thereafter, each pot was maintained in a flooded condition to a depth of 3 cm. Four weeks after the treatment with the active-compound preparation, the herbicidal efficacy and the phytotoxicity towards the rice plants were evaluated, in comparison with untreated control pots, on the following scales.

Herbicidal efficacy

5 — more than 95%
4 — more than 80%
3 — more than 50%
2 — more than 30%
1 — more than 10%
0 — 10% or less

Phytotoxicity towards rice plants

5 — more than 90% (plant completely injured)
4 — more than 50%
3 — more than 30%
2 — 30% or less
1 — less than 10%
0 — 0% (no phytotoxicity)

The test results are shown below in Table A

Table A

| Compound No. | Dosage rate of active compound (kg/ha) | *Echinochloa crus-galli* | *Eleocharis acicularis* | Cyperus sp. | Broadleaved weeds | Phytotoxicity Rice plants |
| --- | --- | --- | --- | --- | --- | --- |
| 1 | 4 | 5 | 5 | 5 | 5 | 0 |
|   | 2 | 5 | 5 | 5 | 5 | 0 |
|   | 1 | 5 | 5 | 5 | 5 | 0 |
| 2 | 4 | 5 | 5 | 5 | 5 | 0 |
|   | 2 | 5 | 5 | 5 | 5 | 0 |
|   | 1 | 5 | 5 | 5 | 4 | 0 |
| 3 | 4 | 5 | 5 | 5 | 5 | 0 |
|   | 2 | 5 | 5 | 5 | 5 | 0 |
|   | 1 | 5 | 5 | 5 | 5 | 0 |
| 4 | 4 | 5 | 5 | 5 | 5 | 0 |
|   | 2 | 5 | 5 | 5 | 4 | 0 |
|   | 1 | 5 | 4 | 5 | 4 | 0 |
| 5 | 4 | 5 | 5 | 5 | 5 | 0 |
|   | 2 | 5 | 5 | 5 | 5 | 0 |
|   | 1 | 5 | 5 | 5 | 4 | 0 |
| 6 | 4 | 5 | 5 | 5 | 5 | 0 |
|   | 2 | 5 | 5 | 5 | 5 | 0 |
|   | 1 | 5 | 5 | 5 | 5 | 0 |
| 7 | 4 | 5 | 5 | 5 | 5 | 0 |
|   | 2 | 5 | 5 | 5 | 5 | 0 |
|   | 1 | 5 | 5 | 5 | 4 | 0 |
| 8 | 4 | 5 | 5 | 5 | 5 | 0 |
|   | 2 | 5 | 5 | 5 | 4 | 0 |
|   | 1 | 5 | 4 | 5 | 4 | 0 |
| 9 | 4 | 5 | 5 | 5 | 5 | 0 |
|   | 2 | 5 | 5 | 5 | 5 | 0 |
|   | 1 | 5 | 5 | 5 | 4 | 0 |
| 10 | 4 | 5 | 5 | 5 | 5 | 0 |
|   | 2 | 5 | 5 | 5 | 5 | 0 |
|   | 1 | 5 | 5 | 5 | 4 | 0 |
| 11 | 4 | 5 | 5 | 5 | 5 | 0 |
|   | 2 | 5 | 5 | 5 | 5 | 0 |
|   | 1 | 5 | 5 | 5 | 4 | 0 |
| 12 | 4 | 5 | 5 | 5 | 5 | 0 |
|   | 2 | 5 | 5 | 5 | 5 | 0 |
|   | 1 | 5 | 5 | 5 | 5 | 0 |
| 13 | 4 | 5 | 5 | 5 | 5 | 0 |
|   | 2 | 5 | 5 | 5 | 5 | 0 |
|   | 1 | 5 | 5 | 5 | 5 | 0 |
| (VI) Comparison compound | 4 | 5 | 5 | 5 | 5 | 4 |
|   | 2 | 5 | 5 | 5 | 4 | 3 |
|   | 1 | 3 | 3 | 3 | 2 | 1 |

NOTE: (VI) The comparison compound is described in U.S. Pat. No. 3,385,689 and has the formula

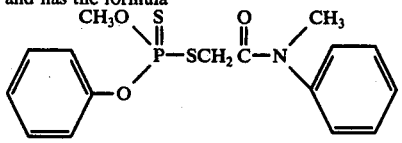

(VI)

EXAMPLE B

Post-emergence treatment under flooded conditions against paddy-field weeds (pot test)

Production of the active-compound preparation

The active compound preparation was obtained in the manner described in Example A.

Test method

Wagner pots (0.0002 are) were charged with soil from a paddy field. Two rice plants (Kinmaze variety) at the two- or three-leaved stage (about 10 cm high) were transplanted into each pot. In addition, *Echinochloa crus-galli*, *Cyperus* sp., *Eleocharis acicularis* L. and seeds of various broadleaved weeds (including *Monochoria vaginalis* Presl, *Rotala indica* Koehne and *Lindernia pyxidaria* L.) were also planted and the whole was maintained in a wet condition.

The active-compound preparation was applied when the *Echinochloa crus-galli* had grown to the two-leaved stage (about 7-9 days after being planted). At the time of the treatment with the active-compound preparation, each pot was flooded to a depth of 6 cm.

After this treatment, water was allowed to leak from each pot for two days at a rate of 2 to 8 cm per day. Thereafter, each pot was maintained in a flooded condition, to a depth of 3 cm. Four weeks after treatment, the herbicidal efficacy and the phytotoxicity towards the rice plants were evaluated, in comparison with untreated control pots, on the scales given in Example A.

The results obtained are given below in Table B.

Table B

| | | Post-emergence treatment under flooded conditions. | | | | |
| | Dosage rate of | Herbicidal Efficacy | | | | |
| Compound No. | active compound (kg/ha) | *Echinochloa crus-galli* | *Eleocharis acicularis* | *Cyperus* sp. | Broadleaved weeds | Phytotoxicity Rice plants |
|---|---|---|---|---|---|---|
| 1 | 4 | 5 | 5 | 5 | 5 | 0 |
|   | 2 | 5 | 5 | 5 | 5 | 0 |
|   | 1 | 5 | 5 | 5 | 5 | 0 |
| 3 | 4 | 5 | 5 | 5 | 5 | 0 |
|   | 2 | 5 | 5 | 5 | 5 | 0 |
|   | 1 | 5 | 4 | 5 | 4 | 0 |
| 12 | 4 | 5 | 5 | 5 | 5 | 0 |
|   | 2 | 5 | 5 | 5 | 5 | 0 |
|   | 1 | 5 | 4 | 5 | 4 | 0 |
| (VI) | 4 | 5 | 5 | 5 | 4 | 4 |
| Comparison | 2 | 3 | 3 | 4 | 2 | 2 |
| compound | 1 | 1 | 2 | 3 | 1 | 0 |

NOTE: (VI): The comparison compound is described in U.S. Pat. No. 3,385,689 and has the following formula

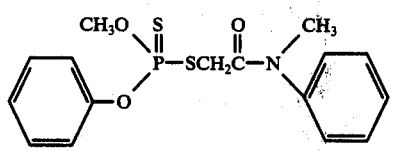

The process for preparing the componds of this invention is illustrated in the following preparative Examples.

EXAMPLE 1

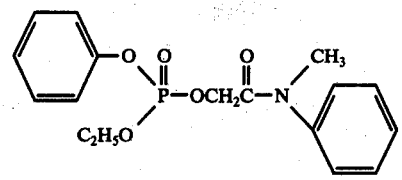

(1)

A solution comprising 4.6 g (0.02 mole) of O-phenyl-O-ethylphosphoryl chloride, 3.3 g (0.02 mole) of glycolic acid-N-methylanilide and 20 ml of toluene was brought to a temperature of 20° - 30° C. The solution was then stirred at this temperature for 1 hour with the addition of 2.1 g (0.02 mole) of triethylamine. The solution was further stirred at 50° - 60° C for 1 hour and then at 80° C for 1 hour. After completion of the reaction, the reaction mixture was cooled to room temperature and washed with water, dilute hydrochloric acid, a 5% aqueous potassium hydroxide solution and water in that order. The organic layer was separated and collected, and then dried with anhydrous sodium sulfate. After removal of toluene by distillation, there was obtained 5.4 g of O-phenyl-O-ethyl-O-(N-methylanilinocarbonylmethyl) phosphate. This final product had a refractive index $n_D^{20}$ of 1.5362.

EXAMPLE 2

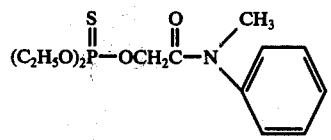

(2)

0.96 g (0.02 mole) of 50% oily sodium hydride was added to a solution comprising 3.77 g (0.02 mole) of O,O-diethylthionophosphoryl chloride, 3.3 g (0.02 mole) of glycolic acid-N-methylanilide and 200 ml of tetrahydrofuran. The resulting solution was stirred at 40° - 45° C for 6 hours. By following the procedure of Example 1 there was obtained 3.3 g of O,O-diethyl-O-

(N-methyl-anilinocarbonyl methyl) phosphorothioate. This final product had a refractive index $n_D^{20}$ of 1.5305.

EXAMPLE 3

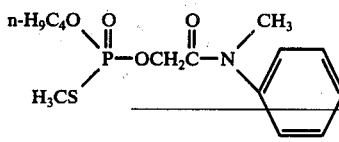

(3)

2.1 g (0.02 mole) of triethylamine were added to a solution comprising 4.16 g (0.02 mole) of O-n-butyl-S-methylthiolphosphoryl chloride, 3.3 g (0.02 mole) of glycol acid-N-methylanilide and 20 ml of toluene. By following the procedure of Example 1 there was obtained 4.9 g of O-n-butyl-S-methyl-O-(N-methyl-anilinocarbonylmethyl) phosphorothioate. This product had a refractive index $n_D^{20}$ of 1.5284.

The compounds shown in Table 1 below were prepared by methods analogous to those of the preceding Examples.

TABLE 1

$$\begin{array}{c} R^1O \diagdown \overset{X}{\underset{\|}{P}} \quad \overset{O}{\underset{\|}{\phantom{P}}} \quad R^3 \\ R^2Y \diagup \phantom{P} -OCH_2C-N \diagdown R^4 \end{array}$$

| Compound No. | R¹ | R² | R³ | R⁴ | X | Y | Refractive index $n_D^{20}$ |
|---|---|---|---|---|---|---|---|
| 4 | $CH_3CH_2CH_2-$ | $CH_3CH_2CH_2-$ | $CH_3-$ | $C_6H_5-$ | O | O | 1.4875 |
| 5 | $CH_3CH_2CH_2CH_2-$ | $CH_3CH_2CH_2CH_2-$ | $CH_3-$ | $C_6H_5-$ | O | O | 1.4822 |
| 6 | $C_6H_5-$ | $C_2H_5-$ | $CH_3-$ | $C_6H_5-$ | S | O | 1.5617 |
| 7 | $C_6H_5-$ | $C_2H_5-$ | $C_2H_5-$ | $C_6H_5-$ | O | O | 1.5360 |
| 8 | $C_6H_5-$ | $C_2H_5-$ | $(CH_3)_2CH-$ | $C_6H_5-$ | O | O | 1.5330 |
| 9 | $C_6H_5-$ | $CH_3CH_2CH_2-$ | $CH_3-$ | $C_6H_5-$ | O | O | 1.5161 |
| 10 | $C_6H_5-$ | $CH_3CH_2CH_2CH_2-$ | $CH_3-$ | $C_6H_5-$ | O | O | 1.5274 |
| 11 | cyclo-$C_6H_{11}-$ | $CH_3-$ | $CH_3-$ | $C_6H_5-$ | O | S | 1.5382 |
| 12 | $C_2H_5-$ | $CH_3CH_2CH_2-$ | $CH_3-$ | $C_6H_5-$ | O | S | 1.5322 |
| 13 | $C_6H_5-$ | $C_2H_5-$ | $CH_3-$ | cyclo-$C_6H_{11}-$ | O | O | 1.5134 |

It will be understood that the specification and examples are illustrative but not limitative of the present invention and that other embodiments within the spirit and scope of the invention will suggest themselves to those skilled in the art.

What is claimed is:

1. Organic (thio)phosphoric acid ester compounds of the formula

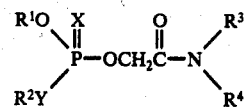

wherein
R¹ is alkyl of from 1 to 6 carbon atoms, cyclohexyl or phenyl,
R² is alkyl of from 1 to 6 carbon atoms,
R³ is alkyl of from 1 to 6 carbon atoms,
R⁴ is cyclohexyl or phenyl,
X is oxygen or sulfur, and
Y is oxygen or sulfur.

2. Organic (thio)phosphoric acid ester compounds as claimed in claim 1 wherein R¹ is alkyl.

3. Organic (thio)phosphoric acid ester compounds as claimed in claim 1 wherein R¹ is cyclohexyl.

4. Organic (thio)phosphoric acid ester compounds as claimed in claim 1 wherein R¹ is phenyl.

5. Organic (thio)phosphoric acid ester compounds as claimed in claim 1 wherein R⁴ is cyclohexyl.

6. Organic (thio)phosphoric acid ester compounds as claimed in claim 1 wherein R⁴ is phenyl.

7. Organic (thio)phosphoric acid ester compounds as claimed in claim 1 wherein X is oxygen.

8. Organic (thio)phosphoric acid ester compounds as claimed in claim 1 wherein X is sulfur.

9. Organic (thio)phosphoric acid ester compounds as claimed in claim 1 wherein Y is oxygen.

10. Organic (thio)phosphoric acid ester compounds as claimed in claim 1 wherein y is sulfur.

11. Organic (thio)phosphoric acid ester compounds as claimed in claim 1 wherein R¹ is C₁-C₄ alkyl, cyclohexyl or phenyl, R² is C₁-C₄ alkyl and R³ is C₁-C₄ alkyl.

12. Organic (thio)phosphoric acid ester compound as claimed in claim 1 of the formula

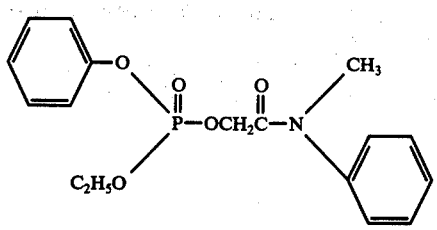

13. Organic (thio)phosphoric acid ester compound as claimed in claim 1 of the formula

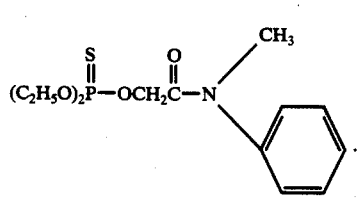

14. Organic (thio)phosphoric acid ester compound as claimed in claim 1 of the formula

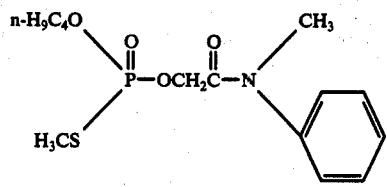

15. Organic (thio)phosphoric acid ester compound as claimed in claim 1 of the formula

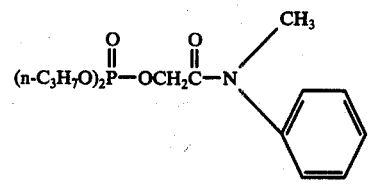

16. Organic (thio)phosphoric acid ester compound as claimed in claim 1 of the formula

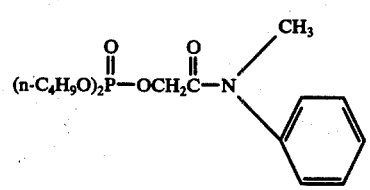

17. Organic (thio)phosphoric acid ester compound as claimed in claim 1 of the formula

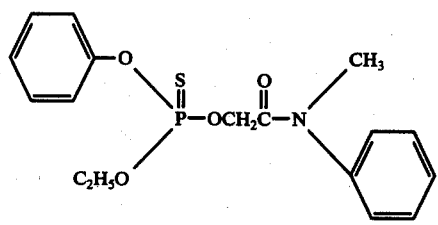

18. Organic (thio)phosphoric acid ester compound as claimed in claim 1 of the formula

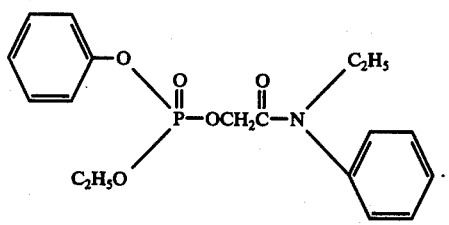

19. Organic (thio)phosphoric acid ester compound as claimed in claim 1 of the formula

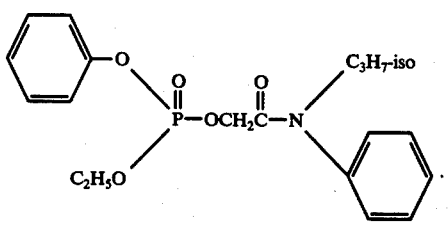

20. Organic (thio)phosphoric acid ester compound as claimed in claim 1 of the formula

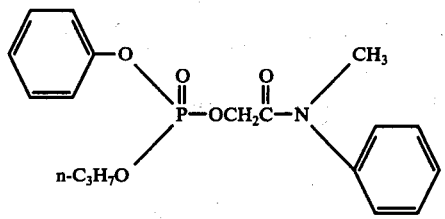

21. Organic (thio)phosphoric acid ester compound as claimed in claim 1 of the formula

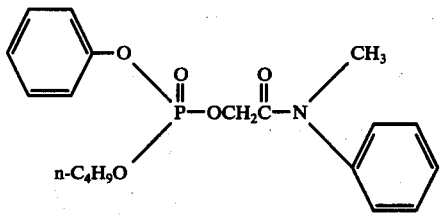

22. Organic (thio)phosphoric acid ester compound as claimed in claim 1 of the formula

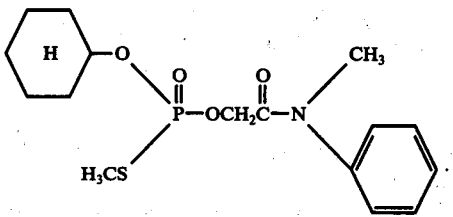

23. Organic (thio)phosphoric acid ester compound as claimed in claim 1 of the formula

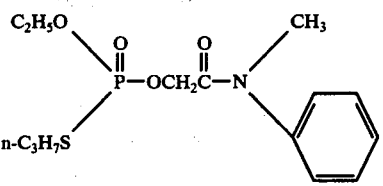

24. Organic (thio)phosphoric acid ester compound as claimed in claim 1 of the formula

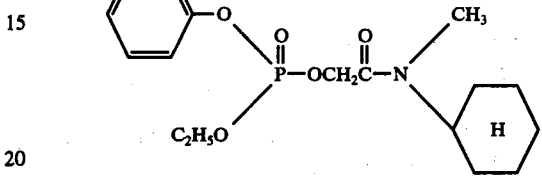

25. Herbicidal composition comprising an agriculturally acceptable carrier and an effective amount of an organic (thio) phosphoric acid ester compound as claimed in claim 1.

26. Method of combatting undesired vegetation which method comprises applying to such vegetation or its habitat effective amounts of an organic (thio)phosphoric acid ester compound as claimed in claim 1.

27. Method of combatting undesired vegetation as claimed in claim 26 wherein said active compound is applied in an amount of from 0.1 to 10 kg per hectare.

28. Method of combatting undesired vegetation as claimed in claim 26 wherein said active compound is applied in an amount of from 0.3 to 6 kg per hectare.

29. Method of combatting undesired vegetation according to claim 26 wherein the effective amount of said organic (thio) phosphoric acid ester is applied to the vegetation or its habitat of rice plants.

30. A process according to claim 29 wherein said organic (thio) phosphoric acid ester is applied prior to emergence of weeds.

31. A method according to claim 29 wherein said organic (thio) phosphoric acid ester is applied after emergence of weeds.

32. A method according to claim 29 wherein said rice is paddy field rice.

* * * * *

UNITED STATES PATENT AND TRADEMARK OFFICE
CERTIFICATE OF CORRECTION

PATENT NO. : 4,059,430
DATED : November 22, 1977
INVENTOR(S) : Masahiro Aya et al It is certified that error appears in the above-identified patent and that said Letters Patent are hereby corrected as shown below:

Column 6, line 36, "compond" should be --compound--.

Column 7, Table A in the column headed "Compound No.", after "6" delete "0".

Column 8, Table A in the column headed "Broadleaved weeds" delete "and has the formula".

Column 9, line 66, "componds" should be --compounds--.

Column 13, line 38, claim 10, line 2, "y" should be --Y--.

Signed and Sealed this

Fourteenth Day of March 1978

[SEAL]

Attest:

RUTH C. MASON
Attesting Officer

LUTRELLE F. PARKER
Acting Commissioner of Patents and Trademarks